(12) United States Patent
Wilkinson

(10) Patent No.: US 6,811,547 B2
(45) Date of Patent: Nov. 2, 2004

(54) NEEDLE SHIELDING ASSEMBLY

(75) Inventor: Bradley Wilkinson, North Haledon, NJ (US)

(73) Assignee: Becton, Dickinson & Company, Franklin Lakes, NJ (US)

( * ) Notice: Subject to any disclaimer, the term of this patent is extended or adjusted under 35 U.S.C. 154(b) by 283 days.

(21) Appl. No.: 10/200,353

(22) Filed: Jul. 22, 2002

(65) Prior Publication Data
US 2004/0015135 A1 Jan. 22, 2004

(51) Int. Cl.[7] .............................................. A61M 5/32
(52) U.S. Cl. ........................ 604/192; 604/263; D24/130
(58) Field of Search ........................ 604/48, 93.01, 604/110, 131, 140, 142, 148, 149, 162, 163, 164.08, 171, 181, 187, 188, 192, 195, 197, 198, 199, 200, 201, 232, 239, 240, 241, 244, 256, 263, 264, 272, 317, 403, 411, 415; 600/573, 576, 577, 583; 206/363, 364, 365, 366, 367, 368, 369, 370, 372; D24/108, 112, 130, 167

(56) References Cited

U.S. PATENT DOCUMENTS

| | | | |
|---|---|---|---|
| 4,416,663 A | * 11/1983 | Hall | 604/198 |
| 4,790,827 A | 12/1988 | Haber et al. | |
| 4,991,601 A | 2/1991 | Kasai et al. | |
| 5,030,209 A | * 7/1991 | Wanderer et al. | 604/198 |
| D323,710 S | 2/1992 | Kasai et al. | |
| 5,139,489 A | 8/1992 | Hollister | 604/192 |
| 5,141,500 A | 8/1992 | Hake | 604/198 |
| 5,154,285 A | 10/1992 | Hollister | 206/365 |
| 5,207,653 A | * 5/1993 | Janjua et al. | 604/192 |
| 5,423,765 A | 6/1995 | Hollister | 604/192 |
| 5,437,639 A | 8/1995 | Malenchek | 604/110 |
| 5,531,703 A | 7/1996 | Skwarek et al. | |
| 5,601,532 A | 2/1997 | Gaba | 604/110 |
| 5,643,219 A | * 7/1997 | Burns | 604/192 |
| 5,807,351 A | 9/1998 | Kashmer | 604/263 |
| 5,980,488 A | 11/1999 | Thorne | 604/110 |
| 6,017,329 A | 1/2000 | Hake | 604/198 |
| 6,298,541 B1 | 10/2001 | Newby et al. | |
| 6,319,232 B1 | 11/2001 | Kashmer | 604/192 |
| D460,183 S | 7/2002 | Wilkinson et al. | |
| D461,244 S | 8/2002 | Niermann | |
| D476,742 S | * 7/2003 | Wilkinson | D24/130 |

* cited by examiner

Primary Examiner—Brian L. Casler
Assistant Examiner—Jennifer Maynard
(74) Attorney, Agent, or Firm—Webb Ziesenheim Logsdon Orkin & Hanson P.C.

(57) ABSTRACT

A needle holder for use with a needle assembly for blood collection is provided. The needle holder includes a generally tubular housing having a needle shield at a first end thereof, and a cutaway notched portion at the other end thereof. A plurality of such needle holders can be stacked in a nested fashion within each other with the cutaway notch of one needle holder accommodating the needle shield of another needle holder.

20 Claims, 6 Drawing Sheets

US 6,811,547 B2

NEEDLE SHIELDING ASSEMBLY

BACKGROUND OF THE INVENTION

1. Field of the Invention

The present invention relates to a needle shielding assembly for use with double-ended needle assemblies commonly used in blood collection procedures. More particularly, the present invention relates to a needle holder which includes a safety shield for use with a double-ended needle for blood collection from a patient.

2. Description of Related Art

Disposable medical devices having piercing elements are typically used for administering a medication or withdrawing a fluid, such as blood collecting needles, fluid handling needles and assemblies thereof. Current medical practice requires that the fluid containers and needle assemblies used in such systems be inexpensive and readily disposable. Consequently, existing blood collection systems, for example, typically employ some form of durable, reusable holder on which detachable and disposable needles and fluid collection tubes may be mounted. A blood collection system of this nature can be assembled prior to use and then disassembled after usage.

A popular design configuration of previously available blood collection systems includes a double-ended needle assembly, an evacuated collection tube, and a holder for maintaining the needle assembly and the collection tube in fixed relation. The double-ended needle assembly, which is also referred to as a cannula, has a bore extending therethrough and a hub near a central region thereof. The evacuated fluid collection tube includes a puncturable stopper at one end thereof. In this type of blood collection system, the holder typically has a housing at one end thereof for receiving the needle assembly. Likewise, the holder also has a hollow body with an opening at an opposite end thereof for receiving the collection tube. The needle assembly is rigidly received within the housing of the holder such that a first end of the needle extends forwardly of the holder for puncturing the vein of a patient. The opposite, second end of the needle extends into the hollow body of the holder. Upon assembly of the blood collection system, the needle assembly is inserted into the housing and the collection tube is inserted through the open end of the hollow body until the second end of the needle pierces the puncturable stopper of the collection tube, thereby allowing fluid communication between the interior of the collection tube and the bore which extends through the needle assembly. To draw a blood specimen from a patient using one of these blood collection systems, the evacuated collection tube is partially inserted into one end of the holder, the first end of the needle is inserted into a patient's vein and the collection tube is fully inserted into the holder such that blood will be drawn through the bore of the needle assembly and into the fluid collection tube. After drawing the specimen, the collection tube is removed so that the blood contained therein can be analyzed and the needle assembly is detached for disposal.

In addition to being capable of accommodating blood collection tubes, the holders of some fluid transfer systems are compatible with fluid containers having a fluid to be injected into a patient. Thus, such holders can be used to inject fluid into, as well as draw blood specimens from, a patient.

In order to reduce the risk of incurring an accidental needle-stick wound, protection of the used needle tip becomes important. With concern about infection and diseases of the blood, methods and devices to enclose the used disposable needle have become very important and in great demand. Many developments have taken place for protecting used needle tips. For example, U.S. Pat. Nos. 5,139,489, 5,154,285 and 5,423,765 disclose needle holders for use with needle assemblies, with the needle holders including pivoting safety shields attached or mounted thereto which can be pivoted about the used needle for protection after use. The entire including the needle holder with the needle assembled therewith and shielded, can then be appropriately discarded.

Such needle holders are readily disposable after use, and therefore large inventories must oftentimes be maintained. This requires the needle holders to be sold in bulk packaging and maintained in large quantities, which increases storage costs.

Accordingly, a need exists for a needle holder which can be used with a needle assembly which can be activated for safety shielding of the needle, which is simple to manufacture, easy to operate, and which is easy to package and store.

SUMMARY OF THE INVENTION

The present invention is directed to a needle holder for use in combination with a needle assembly having a needle cannula with a puncture tip designed for penetration of the body. The needle holder includes a hollow housing having a forward end and a rearward end, and a generally tubular wall extending therebetween. The forward end is adapted to accommodate a needle assembly with a puncture tip extending from the forward end of the housing. The rearward end of the housing is adapted for the insertion of a fluid collection container, such as an evacuated blood collection container. The tubular wall of the housing includes at least one cutaway portion, such as a slot or notch, which extends from the rearward end along a portion of the tubular wall. The needle holder also includes a needle shield which is capable of protectively surrounding the needle cannula of the needle assembly when it is assembled with the housing. The needle holder is designed such that the forward end of a first needle holder is capable of nesting within the rearward end of a second needle holder, with the cutaway portion of the second needle holder accommodating the needle shield of the first needle holder. As such, a plurality of needle holders can be nestably stacked prior to assembly with a needle assembly for use.

Desirably, the needle shield includes an elongated housing having a slot extending along its length for accommodating and protectively engaging the needle cannula, with the needle shield being pivotally engageable with the needle cannula. Preferably, the needle shield is integrally formed with the housing of the needle holder through a living hinge.

Preferably, the rearward end of the housing is flared outwardly. In particularly preferred embodiments, the cutaway portion of the tubular wall and the needle shield are axially aligned along the housing.

The present invention is further directed to a method for packaging a plurality of needle holders designed for use in combination with needle assemblies. Such a method involves providing a plurality of needle holders as set forth above, and stacking the plurality of needle holders such that the forward end of each needle holder is nested within the rearward end of another needle holder, with the needle shield of each needle holder accommodated within the cutaway portion of another needle holder.

In a further embodiment, the needle holder includes a generally tubular hollow housing having a forward end and a flared rearward end, with the housing including a notch extending from the rearward end along a portion of the housing, and with a pivoting elongated needle shield attached to the housing. A plurality of such needle holders can be nestably stacked together, with the needle shield of one needle holder extending through the notch of an adjacent needle holder.

In yet a further embodiment, the present invention is directed to a kit or storage system for a plurality of needle holders, with each of the plurality of needle holders including a hollow housing having a generally tubular wall extending between a forward end and a rearward end, with the tubular wall including a cutaway portion extending from the rearward end along a portion of the tubular wall and with an elongated shield pivotably attached to the forward end of the housing. The plurality of needle holders are nested within each other such that the shield of each needle holder extends within the cutaway portion of an adjacent needle holder.

DETAILED DESCRIPTION

Figure 1:
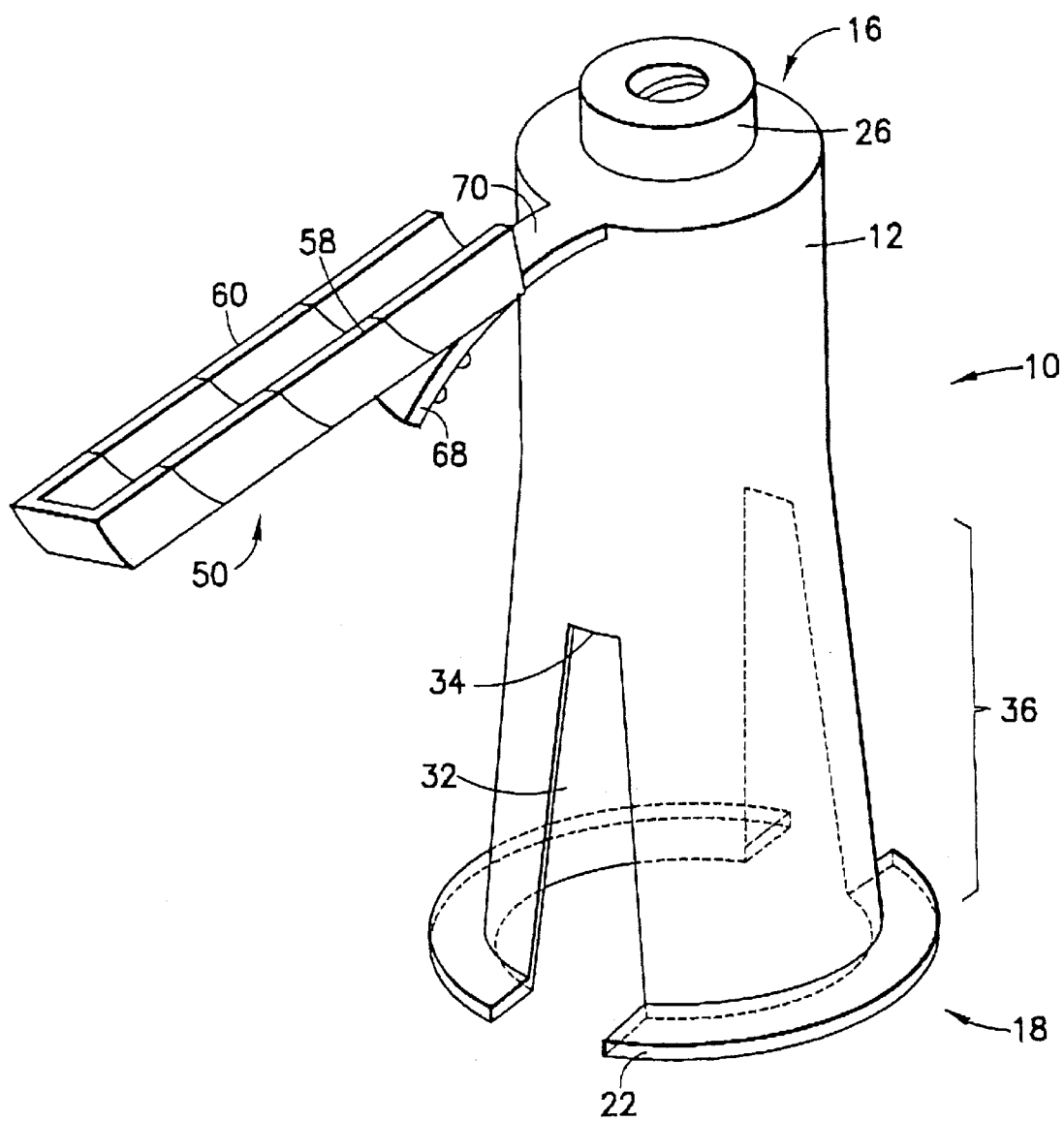
FIG. 1 is a perspective view of a needle holder in accordance with the present invention.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Figure 2:
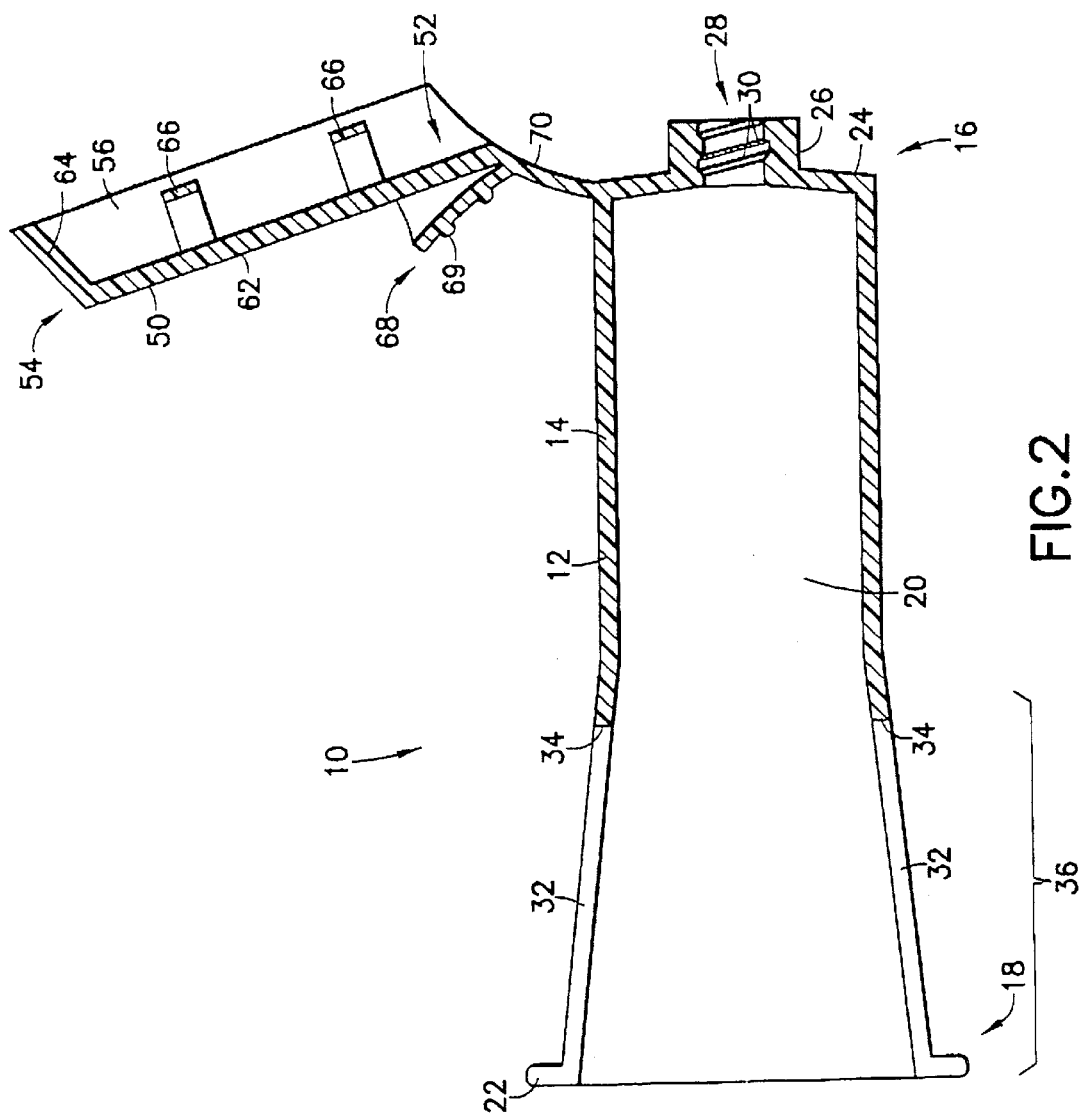
FIG. 2 is a side cross-sectional view of the needle holder of FIG. 1.
Figure 3:
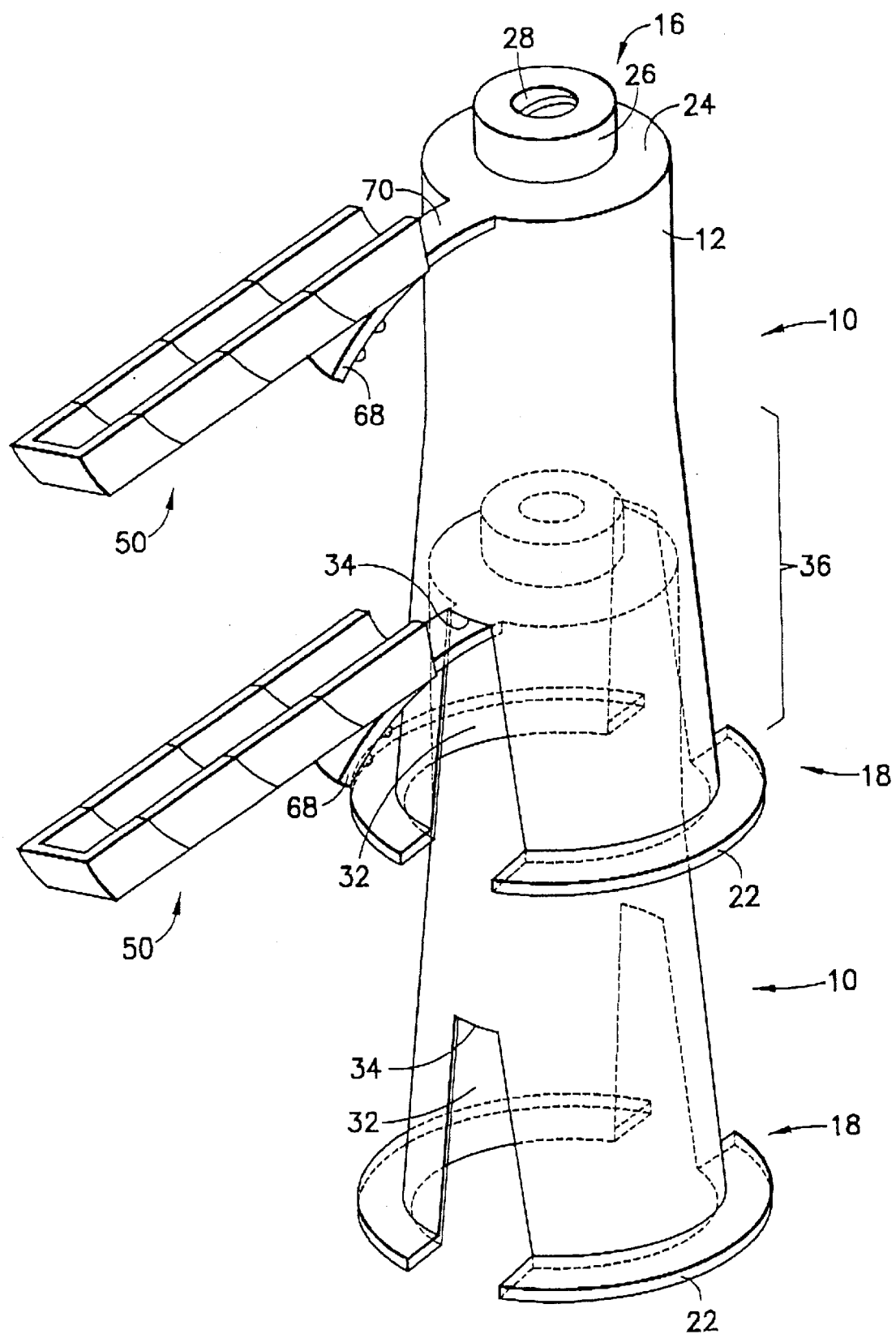
FIG. 3 is a perspective view of a plurality of needle holders of the present invention shown stacked in a nested arrangement.

Referring to the drawings in which like reference characters refer to like parts throughout the several views thereof, FIGS. 1–3 illustrate a needle holder 10 in accordance with the present invention and the related features. As will be described in more detail herein, the needle holder is intended for use, for example, in combination with a needle assembly, such as a double-ended phlebotomy needle, for collecting blood samples.

Needle holder 10 includes a generally tubular or cylindrical housing 12 defined by a tubular wall 14 extending between a forward end 16 and a rearward end 18, with an internal opening 20 extending therethrough. Rearward end 18 of housing 12 is open-ended into an internal opening 20, and may include a flange 22 extending perimetrically outward around the open end at rearward end 18. Forward end 16 of housing 12 includes a forward wall 24 which extends to a shoulder to form a cylindrical neck 26. Neck 26 includes an aperture such as an opening 28 therethrough which extends into internal opening 20 of housing 12. Internal threads 30 may be provided within the opening 28 of neck 26 for threaded engagement with a separate needle assembly to maintain such a needle assembly attached to needle holder 10 during blood collection procedure, as will be described in more detail herein.

Needle holder 10 further includes at least one cutaway portion through tubular wall 14 of housing 12, such as a longitudinal slot or notch 32. Notch 32 extends through tubular wall 14 along a portion of housing 12 from rearward end 18 toward forward end 16. Notch 32 extends to and ends at a forward edge 34, and may narrow from a wider opening at rearward end 18 to a shorter opening at edge 34, or may be of constant width along the entire length of notch 32. Needle holder 10 may include any number of notches extending through tubular wall 14 of housing 12 from rearward end 18, as long as such notches 32 do not deleteriously affect the structural integrity of the tubular shape of needle holder 10. Desirably, needle holder 10 includes a pair of notches 32, as shown in FIGS. 1–3.

Housing 12 of needle holder 10 may further include a portion of tubular wall 14 which flares outwardly toward rearward end 18, such as flared segment 36 depicted in FIGS. 1 and 2. Alternatively, tubular wall 14 of housing 12 may taper outwardly along the entire length thereof from forward end 16 to rearward end 18. Such a taper or flared segment 36 provides housing 12 with a larger diameter at rearward end 18, which is beneficial in stacking and storing a plurality of needle holders 10, as will be discussed in more detail.

Needle holder 10 further includes a needle shield 50 adjacent forward end 16 of housing 12. Needle shield 50 comprises a rearward end 52 and a forward end 54. Forward end 54 of needle shield 50 includes a slot or longitudinal opening 56 formed by sidewalls 58 and 60 that extend downwardly from top section 62 and run substantially opposite of one another in parallel along the length of slot 56 towards a forward endwall 64.

Needle shield 50 may further include an extension which provides a profile for accommodating a user's finger or thumb for pivotal movement of needle shield 50. For example, needle shield 50 may include a tab 68 extending from top section 62. Tab 68 may have an arcuate surface, and may include ribs or bumps 69 on a surface of tab 68 which provide a tactile surface for the user during activation to pivot needle shield 50 to a shielding position.

In particular, needle shield 50 is pivotably connected to needle holder 10 at forward end 16 through a hinge 70. Needle shield 50 is pivotal with respect to needle holder 10, such that when a needle assembly is assembled with needle holder 10, needle shield 50 can protectively encompass or surround the needle cannula of such a needle assembly, as will be discussed in more detail herein.

Needle shield 50 may also include means for trapping such a needle cannula within slot 56, such as a needle cannula lock 66. Such a needle cannula lock 66 may include a resiliently flexible finger portion that extends from an interior portion of top section 62, with a needle engaging barb extending from one side of the finger portion. As such, the needle cannula lock 66 is deflectable to permanently trap a needle cannula within needle shield 50, which prevents movement of needle shield 50 from the shielded position.

Needle shield 50 may be integrally formed with housing 12 of needle holder 10, or may be a separate member which is separately attached to housing 12 of needle holder 10. Desirably, needle shield 50 is integrally formed with housing 12, with hinge 70 as a living hinge connecting needle shield 50 with housing 12.

Needle holder 10 may be constructed of any material known in the art, and is desirably a polymeric material. Preferably, needle holder 10 is constructed of polypropylene.

The overall shape and configuration of needle holder 10 provides the ability to stack a plurality of needle holders in a nestable fashion as shown in FIG. 3. When a pivoting needle shield is attached or used in connection with a conventional needle holder, a number of holders cannot be stacked with each other due to the interference of the pivoting needle shield. In the present invention, notch 32 provides needle holder 10 with a cutaway portion for accommodating the needle shield 50 of a separate needle holder 10. As such, the forward end 16 of one needle holder 10 can be accommodated within the rearward end 18 of a separate needle holder 10, and extend partially within the internal opening 20 of such a separate needle holder 10, as shown in FIG. 3. Needle shield 50 of one needle holder 10 is accommodated within notch 32, and can rest against forward edge 34 of notch 32. Moreover, flared segment 36 of one needle holder 10 provides an enlarged area within internal opening 20 for assisting in accommodating the forward end 16 of a separate needle holder 10. As such, a plurality of needle holders 10 can be stacked in a nested fashion. While FIG. 3 depicts two needle holders 10 in a nested fashion, it is noted that any number of needle holders 10 can be stacked in such a nested fashion.

By providing needle holder 10 as an article which can be stacked in such a nested fashion, packaging and storage space of a plurality of needle holders 10 can be effectively reduced. As such, a plurality of needle holders 10 can be packaged and assembled in a nested fashion, and sold as a kit, thereby reducing the bulk packaging typically associated with non-nestable needle holders. The present invention therefore also relates to a method for packaging a plurality of needle holders 10, by stacking the needle holders with the forward end 16 of each needle holder 10 nested within the rearward end 18 of another needle holder 10, with the needle shield 50 of each needle holder 10 accommodated within the notch 32 of another needle holder 10.

Desirably, needle shield 50 and notch 32 are axially aligned with each other based on the longitudinal axis of needle holder 10. Such axial alignment provides for a further reduction in packaging, in that when a plurality of needle holders 10 are stacked and nested with each other, all of the needle shields 50 extend in the same direction, generally perpendicular to the longitudinal axis of nested needle holders 10, as shown in FIG. 3.

Figure 4:
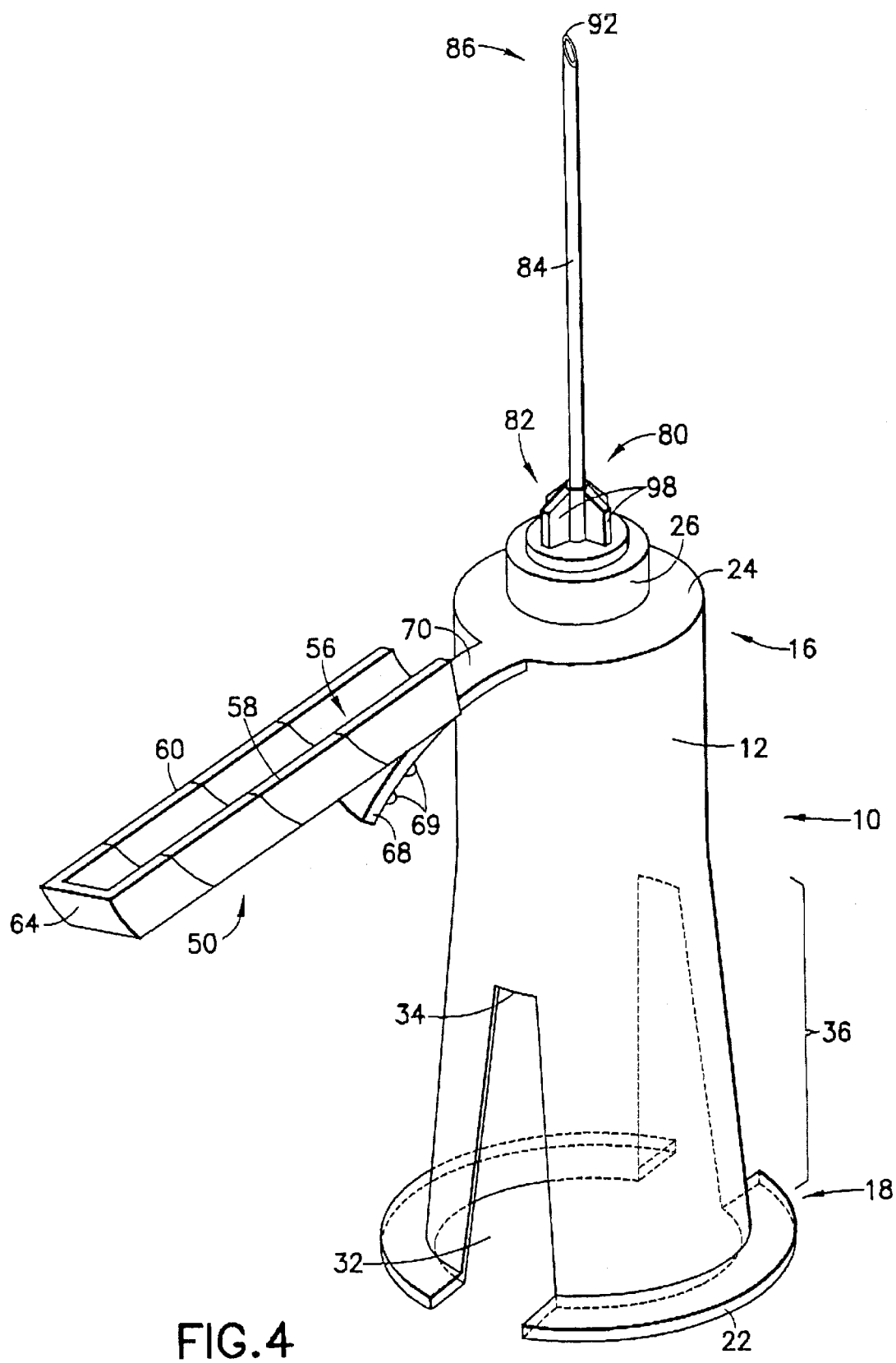
FIG. 4 is a perspective view of a needle holder in accordance with the present invention shown in combination with a needle assembly.
Figure 5:
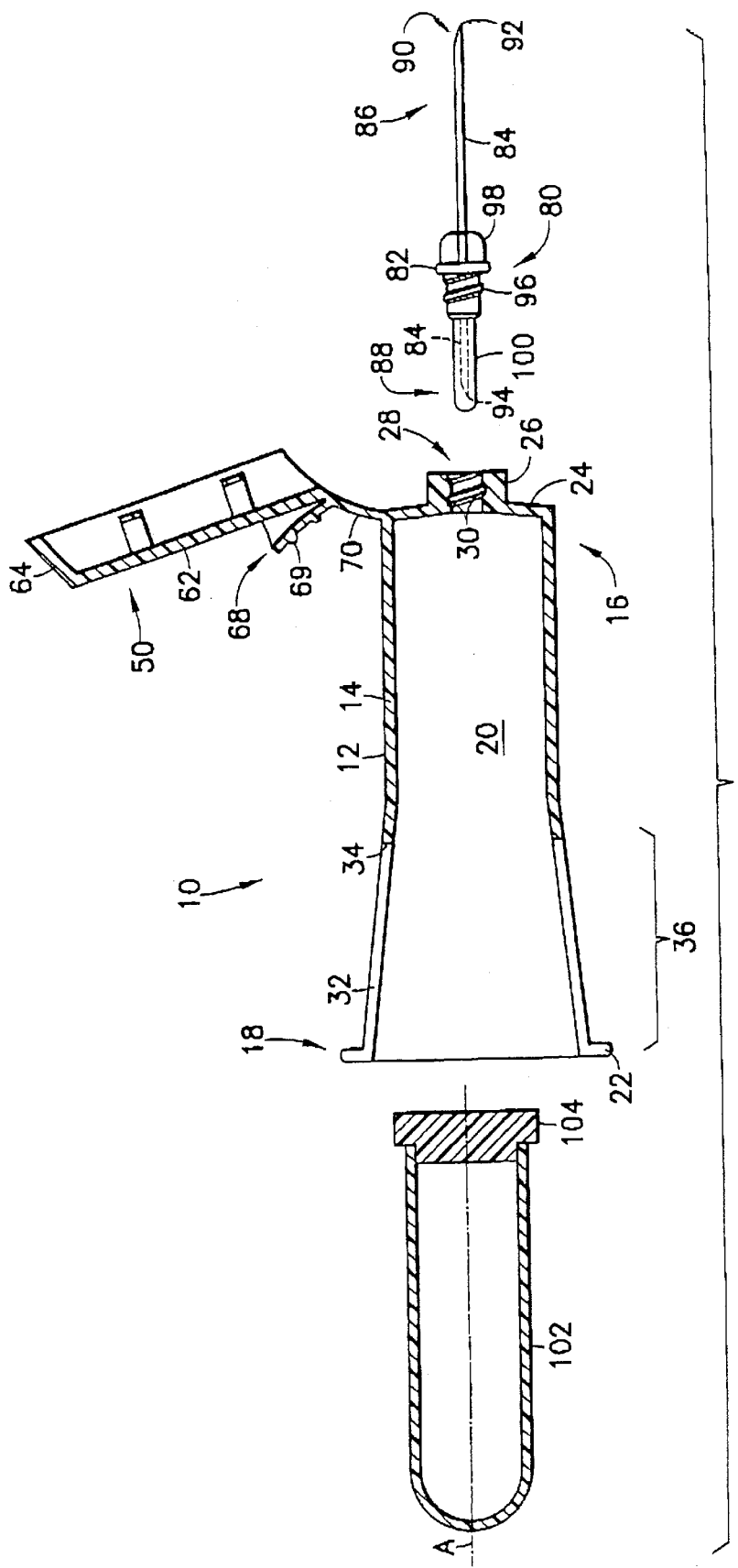
FIG. 5 is an exploded sectional view of the needle holder of the present invention shown in combination with a needle assembly and an evacuated collection tube.
Figure 6:
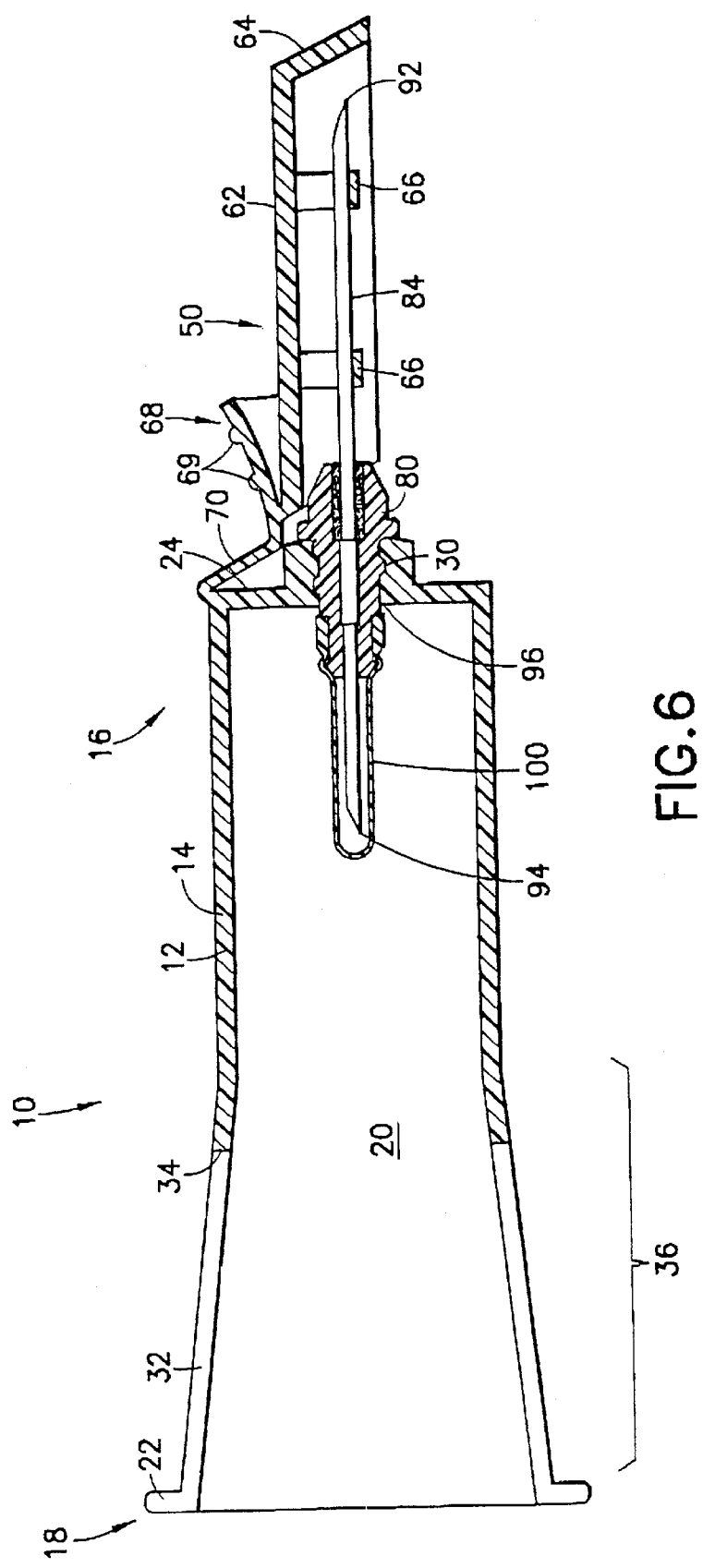
FIG. 6 is a cross-sectional view of the needle holder of the present invention shown in combination with a needle assembly with the needle shield in a shielded position covering the needle.

FIGS. 4–6 depict the needle holder 10 of the present invention in use in connection with a conventional double-ended needle assembly 80. Needle assembly 80 includes a hub 82 having a needle cannula 84 extending therethrough. Needle cannula 84 has a forward end 86 and an opposing rearward end 88. The needle cannula 84 defines an internal lumen 90 extending through the needle cannula 84 from forward end 86 to rearward end 88. Forward end 86 of needle cannula 84 is beveled to define a sharp puncture tip at an intravenous puncture tip 92. Intravenous puncture tip 92 is provided for insertion into a patient's blood vessel, such as a vein, and is, therefore, designed to provide ease of insertion and minimal discomfort during venipuncture. Rearward end 88 of needle cannula 84 includes a non-patient puncture tip 94. Non-patient puncture tip 94 includes a sharp puncture tip which is provided for puncturing of an evacuated tube for example during a blood collection procedure, such as collection tube 102 having a piercable closure 104 as shown in FIG. 5. An elastomeric sleeve 100 covers the non-patient puncture tip 94, extending from hub 82 about the rearward end 88 of needle cannula 84. Elastomeric sleeve 100 is deflectable and puncturable by non-patient puncture tip 94 when pressure is exerted therebetween by forcing a piercable closure 104 of collection tube 102 thereagainst, as is common in a blood collection procedure.

Desirably, needle assembly 80 is a separate member which is packaged in a sterile environment, including needle covers (not shown) extending about both the forward end 86 and rearward end 88 of needle assembly 80. Such a separately packaged needle assembly can be assembled with needle holder 10 just prior to use in a blood collection procedure. As such, hub 82 of needle assembly 80 includes means for mating with needle holder 10, such as external threads 96. Such threads 96 can be threadably mated with internal threads 30 within opening 28 of needle holder 10 to attach needle assembly 80 to needle holder 10 for use. As such, needle assembly 80 can be axially aligned along axis A of needle holder 10. Hub 82 may further include ribs 98, which can provide for frictional engagement of a packaging needle cover (not shown).

When needle assembly 80 is assembled with needle holder 10, needle shield 50 can be pivoted away from needle cannula 84 through hinge 70 to a retracted position, as shown in FIG. 4, thereby permitting access of needle cannula 84 for a blood collection procedure. After use in such a procedure, the user can exert a force, such as by applying pressure on tab 68 with the user's thumb, such that needle shield 50 can be moved into a shielding position as shown in FIG. 6 in which the forward end 86 of needle cannula 84 is encompassed within slot 56 of needle shield 50. In addition, the needle cannula lock 66 can engage needle cannula 84, thereby preventing any further pivotal movement of needle shield 50 to re-expose needle cannula 84. The needle safety device can then be safely discarded.

While the needle assembly of the present invention has been described in terms of one embodiment for use in connection with a blood collection system, it is further contemplated that the needle assembly could be used with other medical procedures, such as in conjunction with conventional intravenous infusion sets, which are well-known in the art for use with needle assemblies.

What is claimed:

1. A needle holder for use in combination with a needle assembly having a needle cannula with a puncture tip designed for penetration of the body, said needle holder comprising:

a hollow housing having a forward end and a rearward end and a generally tubular wall extending therebetween, said forward end being adapted to accommodate a needle assembly such that a puncture tip of said needle assembly extends from said forward end of said housing, said rearward end adapted for the insertion of a fluid collection container, said tubular wall of said housing including a cutaway portion extending from said rearward end along a portion of said tubular wall; and a needle shield attached to said housing and capable of protectively surrounding the needle cannula of said needle assembly when the needle assembly is assembled with said housing;

wherein said forward end of a first needle holder is capable of nesting within the rearward end of a second needle holder, with said cutaway portion of said tubular wall of such second needle holder accommodating said needle shield of such first needle holder.

2. A needle holder as in claim 1, wherein said needle shield comprises an elongated housing having a slot extending along the length thereof, said slot accommodating said needle cannula when the needle assembly is assembled with said housing and the needle shield protectively engages said needle cannula.

3. A needle holder as in claim 1, wherein said needle shield is pivotally engageable with said needle cannula.

4. A needle holder as in claim 1, wherein said needle shield is a separate member which is separately attached to said needle holder.

5. A needle holder as in claim 1, wherein said needle shield includes a tab for accommodating a user's finger to move said needle shield to a position protectively surrounding the needle cannula.

6. A needle holder as in claim 1, wherein said needle shield is integrally formed with said needle holder through a living hinge.

7. A needle holder as in claim 1, wherein said rearward end of said housing is flared outwardly.

8. A needle holder as in claim 1, wherein said cutaway portion of said tubular wall and said needle shield are axially aligned with respect to said housing.

9. A needle holder as in claim 1, wherein said forward end of said housing includes an aperture for accommodating said needle assembly therethrough.

10. A needle holder as in claim 9, wherein said aperture includes threads for threaded engagement with said needle assembly.

11. A method for packaging a plurality of needle holders designed for use in combination with needle assemblies comprising:
 a) providing a plurality of needle holders each comprising a generally tubular hollow housing having: a forward end adapted to accommodate a needle assembly extending therefrom; a rearward end adapted for the insertion of a fluid collection container therethrough; a cutaway portion extending from said rearward end along a portion of said tubular housing; and a needle shield adjacent the forward end, said needle shield being capable of protectively surrounding the needle assembly when the needle assembly is assembled with said tubular housing;
 b) stacking said plurality of needle holders such that said forward end of each of said plurality of needle holders is nested within the rearward end of another of said plurality of needle holders, with said needle shield of each of said plurality of needle holders accommodated within said cutaway portion of another of said plurality of needle holders.

12. A method as in claim 11, wherein said needle shield is integrally formed with said tubular housing through a living hinge.

13. A method as in claim 11, wherein said rearward end of said tubular housing is flared outwardly.

14. A method as in claim 11, wherein said cutaway portion of said tubular housing and said needle shield are axially aligned.

15. A needle holder for use in combination with a needle assembly having a needle cannula, said needle holder comprising:
 a generally tubular hollow housing having a forward end and a flared rearward end, said forward end adapted to accommodate said needle assembly with at least a portion of said needle cannula extending from said forward end, said rearward end adapted for the insertion of a fluid collection container, said housing including a notch extending from said rearward end along a portion of said housing; and
 a pivoting elongated needle shield attached to said housing, said needle shield capable of pivoting to encompass said needle cannula when said needle assembly is assembled with said needle holder;
 wherein a plurality of said needle holders can be nestably stacked together, with the needle shield of one of said plurality of needle holders extending through the notch of an adjacent one of said plurality of needle holders.

16. A needle holder as in claim 15, wherein said needle shield is pivotable from a first position extending away from an axis defining said needle holder to a second position in alignment with the axis defining said needle holder, and wherein said needle shield is in said first position when said plurality of needle holders are stacked.

17. A needle holder as in claim 15, wherein said notch and said needle shield are axially aligned with each other.

18. A needle holder as in claim 15, wherein said forward end of said housing includes an aperture for accommodating said needle assembly therethrough.

19. A needle holder as in claim 18, wherein said aperture includes threads for threaded engagement with said needle assembly.

20. A kit comprising:
 a plurality of needle holders, each of said plurality of needle holders comprising a hollow housing having a generally tubular wall extending between a forward end and a rearward end, said tubular wall including a cutaway portion extending from said rearward end along a portion of said tubular wall, and an elongated shield pivotably attached to said forward end of said housing,
 said plurality of needle holders being nested within each other such that said shield of each of said plurality of needle holders extends within said cutaway portion of an adjacent one of said plurality of needle holders.

* * * * *